(12) United States Patent
Buhler et al.

(10) Patent No.: US 9,466,498 B2
(45) Date of Patent: Oct. 11, 2016

(54) CMOS GAS SENSOR AND METHOD FOR MANUFACTURING THE SAME

(71) Applicant: Sensirion AG, Stafa (CH)

(72) Inventors: Johannes Buhler, Uster (CH); Cyrill Kuemin, Rapperswil (CH)

(73) Assignee: Sensirion AG, Stafa (CH)

( * ) Notice: Subject to any disclaimer, the term of this patent is extended or adjusted under 35 U.S.C. 154(b) by 313 days.

(21) Appl. No.: 14/160,986

(22) Filed: Jan. 22, 2014

(65) Prior Publication Data

US 2014/0208830 A1 Jul. 31, 2014

(30) Foreign Application Priority Data

Jan. 31, 2013 (EP) .................................... 13405019

(51) Int. Cl.
| | |
|---|---|
| *G01N 7/00* | (2006.01) |
| *G01N 9/00* | (2006.01) |
| *H01L 21/00* | (2006.01) |
| *H01L 23/48* | (2006.01) |
| *H01L 23/52* | (2006.01) |
| *H01L 29/40* | (2006.01) |
| *H01L 21/285* | (2006.01) |
| *G01N 27/12* | (2006.01) |

(52) U.S. Cl.
CPC ....... *H01L 21/28556* (2013.01); *G01N 27/122* (2013.01)

(58) Field of Classification Search
None
See application file for complete search history.

(56) References Cited

U.S. PATENT DOCUMENTS

| | | | | |
|---|---|---|---|---|
| 4,512,871 A | * | 4/1985 | Kato ................. | G01N 27/4067 204/427 |
| 4,528,086 A | * | 7/1985 | Kato ................. | G01N 27/4067 204/409 |
| 7,154,372 B2 | | 12/2006 | Vanha et al. | |
| 7,495,300 B2 | * | 2/2009 | Gardner ............... | G01N 27/128 257/252 |
| 7,849,727 B2 | * | 12/2010 | Gardner ............. | G01N 33/0031 73/31.06 |
| 7,998,546 B2 | * | 8/2011 | Wisnudel .............. | G09F 3/0291 283/72 |
| 9,080,907 B2 | * | 7/2015 | Haneef ................. | G01F 1/6845 |
| 2014/0318960 A1 | * | 10/2014 | Huang ............... | G01N 27/4073 204/406 |

FOREIGN PATENT DOCUMENTS

| | | | |
|---|---|---|---|
| EP | 2278309 | | 1/2011 |
| GB | 2464016 | | 4/2010 |
| JP | 2002116171 A | * | 4/2002 |
| WO | 9519563 | | 7/1995 |

OTHER PUBLICATIONS

S. Ali, et al., "High Temperature SOI CMOS Tungsten Micro-Heaters", IEEE Sensors, EXCO, Daegu, Korea, Oct. 22-25, 2006, pp. 847-850.
M. Graf, et al., "CMOS Microhotplate Sensor System for Operating Temperatures Up to 500C", Sensors and Actuators B, Elsevier, vol. 117, 2006, pp. 346-352.
Y. Li, et al., "Monolithic CMOS Multi-Transducer Gas Sensor Microsystem for Organic and Inorganic Analytes", Sensors and Actuators B, Elsevier, vol. 126, 2007, pp. 431-440.

\* cited by examiner

*Primary Examiner* — Michael A Lyons
*Assistant Examiner* — Jermaine Jenkins
(74) *Attorney, Agent, or Firm* — Cooper & Dunham LLP

(57) ABSTRACT

A CMOS gas sensor comprises a membrane (13) extending over an opening (12) of a silicon substrate (1). A patch (2) of sensing material is arranged on the membrane (13) and in contact with electrodes (3) of platinum. A heater (5) of tungsten is located in or on the membrane (13) at the location of the patch (2) of metal-oxide sensing material. Combining platinum electrodes (3) with a tungsten heater (5) on top of a CMOS structure provides a gas sensor of high reliability and stability.

15 Claims, 2 Drawing Sheets

CMOS GAS SENSOR AND METHOD FOR MANUFACTURING THE SAME

TECHNICAL FIELD

The invention relates to gas sensor having a silicon substrate and CMOS circuitry integrated on the silicon substrate. The gas sensor further comprises an opening extending through the substrate and a membrane extending over this opening. A patch of sensing material is arranged on the membrane, and electrodes are provided on the membrane in contact with the patch of sensing material. The membrane forms a hot plate heated by a tungsten heater arranged in or on the membrane at the location of the patch.

BACKGROUND ART

A sensor of this type is described in GB 2464016. It uses a patch of metal oxide that changes its electrical conductance depending on the composition of the gas that it is exposed to. The patch is heated to a suitable operating temperature, typically in the range of 300° C.-600° C. The patch is arranged on a membrane for thermal insulation and thermally coupled to a tungsten heater.

DISCLOSURE OF THE INVENTION

It is an object of the present invention to provide an improved design and manufacturing method for such a gas sensor that has high signal stability.

This object is achieved by the sensor device and the method of the independent claims.

Accordingly, the gas sensor comprises a silicon substrate with CMOS circuitry integrated on the silicon substrate. An opening extends through the substrate, and a membrane extends over this opening in order to form a hotplate for receiving a patch of sensing material. Electrodes are arranged on the membrane and are in electrical contact with the patch of sensing material in order to measure a signal indicative of the sensing material's electrical conductivity. For heating the sensor material, a heater of tungsten is arranged in or on the membrane at the location of the patch of sensing material.

The electrodes are of platinum. While electrodes of most other materials, such as tungsten or aluminum, tend to cause drift when being used in a gas sensor of this type, it is found that platinum electrodes are highly stable (chemically inert) and therefore reduce the device's tendency to drift. At the same time, platinum electrodes are well able to withstand the high temperatures on the hotplate.

In contrast to this, the heater is made of tungsten, which also exhibits high temperature stability and is robust against electromigration. Tungsten has a high conductivity, which allows to generate a high heating power over a small heater cross section with low supply voltage—this is particularly advantageous for low-voltage devices, e.g. for mobile applications.

The sensor is advantageously manufactured by a method comprising the following steps:

a) forming the tungsten heater by depositing and structuring a layer of tungsten and b) forming the electrodes by depositing and structuring a layer of platinum.

Advantageously, the gas sensor further comprises a platinum temperature sensor arranged on the membrane. The electrodes and the temperature sensor can be commonly formed in a single step by structuring the same platinum layer.

Further, the device can be equipped with at least one heat spreading structure of platinum or tungsten, in addition to the electrodes and the heater, i.e. the heat spreading structure is neither arranged to carry the heating current, nor it is required as electrode. Such a heat spreading structure improves the temperature homogeneity over the patch of sensing material. In order to avoid thermal losses, the heat spreading structure should not extend over the edge of the membrane, i.e. it should not extend over the bulk of the silicon substrate. Advantageously, the heat spreading structure should not extend further than the region heated by the heater.

The layer of platinum is advantageously applied by sputtering.

Ion etching is advantageously used for forming structures with inclined edges from the platinum layer. This etching technique allows to form such inclined edges, i.e. edges that extend under an inclined angle≠90°, in particular between 30 and 60°, to the surface of the substrate. Such faceted edges make it easier to apply a passivating cover layer over the platinum layer.

The tungsten heater (and any further tungsten structure) is advantageously formed by a Damascene process that comprises the following steps:

a) forming trenches (i.e. recesses) in a surface of the substrate;

b) applying the layer of tungsten to said surface; and c) removing the layer of tungsten where it does not extend into the trenches.

This process allows to form laterally fine structures of large thickness. Further, it yields a flat surface that allows to keep the subsequently applied layers thin, thus allowing to manufacture a very thin membrane with low thermal conductivity. Also, this flat surface allows to form very fine platinum structures above it using photolithography.

The above step of removing the layer of tungsten where it does not extend into the trenches is advantageously carried out by means of polishing the tungsten layer, in particular by using chemical mechanical polishing, also called chemical-mechanical planarization.

The layer of tungsten is advantageously manufactured using chemical vapor deposition.

Other advantageous embodiments are listed in the dependent claims as well as in the description below.

BRIEF DESCRIPTION OF THE DRAWINGS

The invention will be better understood and objects other than those set forth above will become apparent from the following detailed description thereof. Such description makes reference to the annexed drawings, wherein.

Note: The drawings are not to scale.

MODES FOR CARRYING OUT THE INVENTION

Definitions

Terms indicating a vertical direction or arrangement, such as "top", "bottom", "above" or "below" relate to a frame of reference where the batch of material layers forming the membrane are arranged on top, i.e. above, the substrate. In other words, the substrate is arranged, by definition, below the material layers and the membrane is located on top of the opening extending through the substrate.

The term "lateral" is used to describe directions parallel to the top and bottom surfaces of the semiconductor substrate.

The term "at a level above" is used in the sense that if a structure A is at a level above a structure B, then structure A is arranged in a material layer that was applied to the top surface of the substrate after forming structure B. Structure A may, however, be laterally offset in respect to structure B.

The term "tungsten" as used herein is to be understood as designating pure tungsten as well as any material, in particular an alloy, comprising at least 90%, in particular at least 95%, of tungsten.

The term "platinum" as used herein is to be understood as designating pure platinum as well as any material, in particular an alloy, comprising at least 90%, in particular at least 95%, of platinum.

Figure 1:
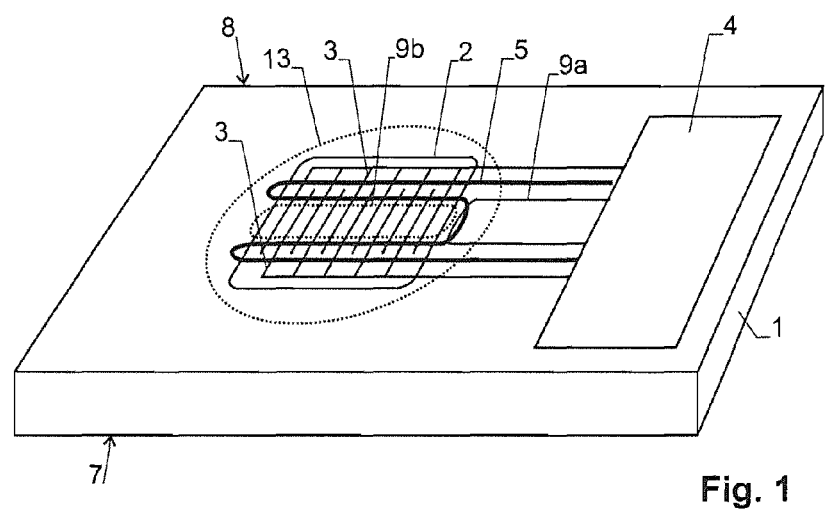
FIG. 1 shows a view of a gas sensor.

The Device:

FIG. 1 shows a gas sensor adapted to generate a signal indicative of the concentration of at least one gaseous analyte in a gaseous carrier, such as alcohol in air. It comprises a semiconductor substrate 1. A sensor material, whose electrical properties depend on the concentration of the analyte, is applied to substrate 1 in a patch 2. For example, patch 2 consists of a granular layer of tin oxide, or of another material whose electrical resistance depends on the presence and concentration of various compounds in the surrounding atmosphere. This type of device is e.g. described in GB 2464016 or in WO 95/19563.

Patch 2 is in electrical contact with at least a pair of interdigitated platinum electrodes 3, which are connected to processing circuitry 4. Processing circuitry 4 is implemented as CMOS circuitry integrated on semiconductor substrate 1 and can e.g. comprise active components, such as transistors, at least one amplifier, at least one analog/digital converter, and/or interface circuitry, etc.

The sensor device further comprises a tungsten heater 5 positioned at the location of patch 2 in order to heat patch 2 to its operating temperature, which, for tin oxide, is e.g. typically at least 300° C.

The device can also be equipped with a temperature sensor 9a for measuring the temperature of the membrane 13 (see below). This temperature sensor 9 is advantageously a platinum temperature sensor formed by a platinum conductor extending over membrane 13.

Finally, the device can be equipped with a heat spreading structure as schematically indicated under reference number 9b. This is a structure of platinum or tungsten formed in at least one of the metal layers laterally extending within the membrane 13 designed to homogeneously spread the heat of heater 5 over the membrane. In the example of FIG. 1, heat spreading structure 9b is formed in the tungsten layer of heater 5. Alternatively, or in addition thereto, it can be formed in the platinum layer that is used for manufacturing the electrodes 3.

Figure 2:
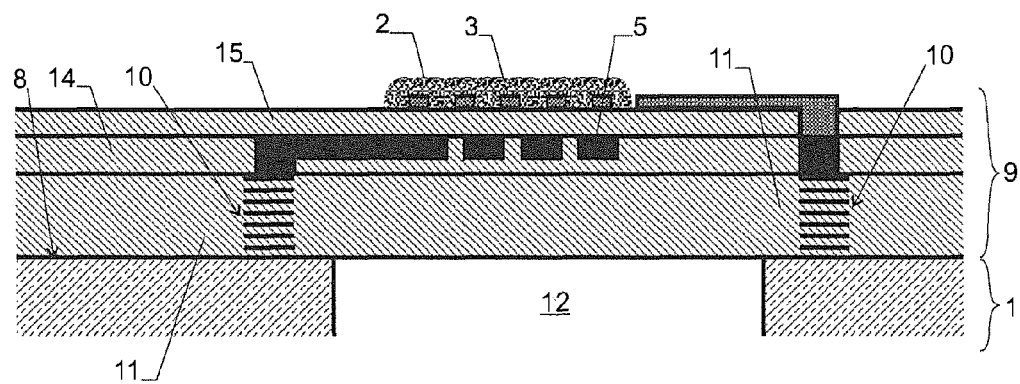
FIG. 2 shows a sectional view of the gas sensor.

FIG. 2 shows a sectional view of this type of device. As can be seen, semiconductor substrate 1 comprises a bottom surface 7 (cf. FIG. 1) and a top surface 8. A batch 9 of material layers is applied to top surface 8 and typically comprises a plurality of structured dielectric layers and a plurality of structured metal layers.

A bottommost part 10 of the various metal layers is typically of aluminum (or AlCu or copper) and forms interconnects of the CMOS circuitry. In FIG. 2, the metal layers 10 are only shown schematically. They are separated by dielectric layers, typically $SiO_2$ layers, which are generally denoted by reference number 11.

Parts of the layers of batch 9 extend over an opening 12 in semiconductor substrate 1 and form a membrane 13. Membrane 13 can have circular or rectangular shape or any other suitable shape.

Advantageously, and in order to reduce the thermal conductance of membrane 13, none of the metal layers 10 extends into membrane 13.

Batch 9 can further comprise a layer of SiN (not shown) under tensile stress, which extends at least over membrane 13 and is anchored laterally outside membrane 13. The tensile stress in this layer can be at least sufficiently large to exceed the compressive stress in the rest membrane 13, which leads to a total tensile stress in the membrane. As described in U.S. Pat. No. 7,154,372, such a tensile layer can be used to prevent the membrane from buckling.

Heater 5 is formed by structuring a tungsten layer into at least one metal conductor, which is located in a $SiO_2$ layer (or other dielectric layer) 14 on membrane 13. As seen in FIG. 1, the metal conductor can e.g. follow a meandering path. Layer 14 is arranged on the SiN layer.

A dielectric layer 15, e.g. $SiO_2$, is arranged on top of the layer of heater 5 and electrically insulates the same from a platinum layer forming the electrodes 3 and temperature sensor 9.

A protective dielectric layer can be applied to the top of the device (not shown).

The patch 2 is arranged on top of the electrodes 3 and in contact therewith.

Manufacturing Process:

FIGS. 3-6 show a method for manufacturing the sensor device.

In a first step, silicon substrate 1 is covered, at its top surface 8, with the dielectric layers 11 as well as with the metal layers 10 in a series of steps as known in the art of CMOS semiconductor device manufacture. For example, a first $SiO_2$-layer is applied to top surface 8, and then the first metal layer is applied onto the first $SiO_2$-layer and structured using photolithography. Then, a second $SiO_2$-layer is applied, and the second metal layer is applied thereto and structured, etc.

Figure 3:
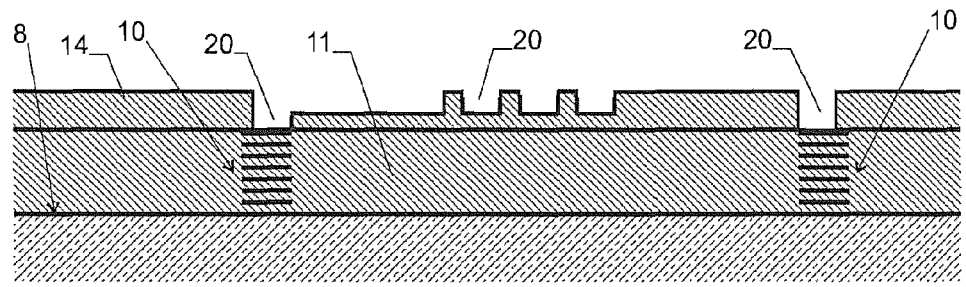
FIG. 3 shows a first step in a manufacturing process of the gas sensor.
Figure 4:
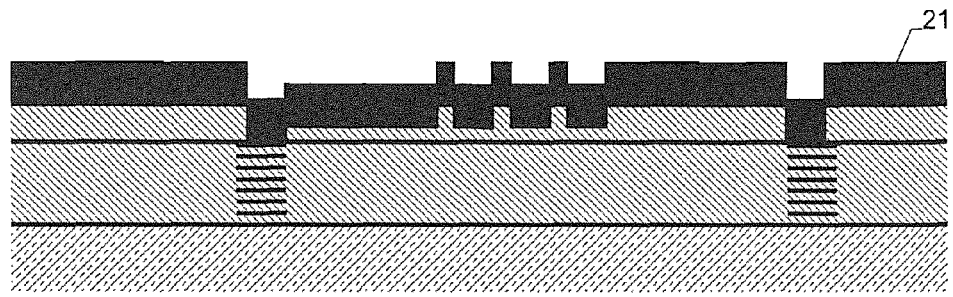
FIG. 4 shows a second step in a manufacturing process of the gas sensor.
Figure 5:
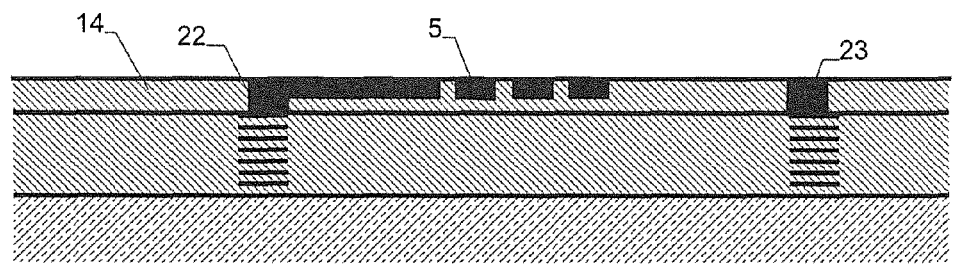
FIG. 5 shows a third step in a manufacturing process of the gas sensor.

After applying the metal layers 10 and the dielectric layers 11, the tungsten layer for heater 5 is applied and structured using a Damascene process illustrated in FIGS. 3, 4 and 5. This type of process is typically known for structuring tungsten or copper interconnects.

First, dielectric layer 14, e.g. $SiO_2$, is applied to the top surface of the device, and trenches 20 (i.e. recesses) are formed therein at the locations where heater 5 and any further tungsten structures are to be formed. At those locations where the tungsten structures or the platinum structures (to be formed layer) are to contact the metal layers 10, the trenches 20 reach all the way to one of the metal layers 10.

In a next step, and as shown in FIG. 4, a layer 21 of tungsten is applied by means of chemical vapor deposition. The thickness of the tungsten layer 21 is between 100 and 1000 nm, in particular between 200 and 600 nm.

The top surface of this layer is then polished, as shown in FIG. 5, using chemical-mechanical planarization, a process known to the skilled person. In this process, the top section of tungsten layer 21 is removed in order to form a flat surface approximately at the top level (or somewhat below the original top level) of dielectric layer 14. Hence, all of tungsten layer 21 is removed except those parts that are located in one of the trenches 20, thereby forming the structure of heater 5, vias 22 for connecting heater 5 to one at least of the metal layers 10, and a bottom section 23 of vias that will connect the structures of the platinum layer to at least one of the metal layers 10.

As mentioned, the described Damascene process allows to manufacture laterally fine but vertically thick structures of tungsten.

Heater 5 advantageously has a thickness of at least 150 nm, which allows to manufacture a heater of low resistivity suitable to be operated at low operating voltages of e.g. 1.8 V or less. Hence, the thickness of heater 5 and therefore the depth of the trenches 20 at the location of heater 5 should be at least 150 nm.

The lateral distance of neighbouring tungsten structures that can be manufactured in this manner can be very small, e.g. smaller than 5 μm, in particular smaller than 3 μm. This again makes the Damascene process very suitable for the present application.

A further advantage of the Damascene process is the resulting excellent step coverage at the location of the tungsten-CMOS interconnects, which avoids electromigration and therefore allows high operating temperatures (>300° C.).

Figure 6:
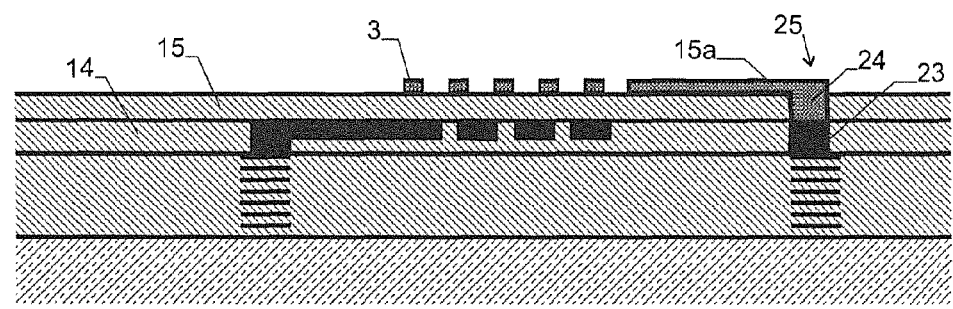
FIG. 6 shows a fourth step in a manufacturing process of the gas sensor.

Now, as shown in FIG. 6, dielectric layer 15, e.g. $SiO_2$, is applied and etched to form openings 15a at the locations of the future vias for connecting the platinum structures to the tungsten structures. Then, a platinum layer is sputtered onto dielectric layer 15 and structured e.g. using photolithographic masking and reactive ion etching or lift-off techniques.

Thanks to the flat surface that has been prepared by the Damascene process for manufacturing the tungsten structures, very fine platinum structures can be manufactured with conventional photolithographic structuring processes. In particular if the surface is not so flat, e.g. because the tungsten layer has been structured using other techniques, the process for structuring the platinum layer advantageously uses anisotropic etching, in particular reactive ion etching, and/or a preparatory milling step, or lift-off techniques.

The thickness of the platinum layer and therefore the electrodes 3 is advantageously small, e.g. less than 200 nm, in particular less than 100 nm because platinum (which is a noble metal) is hard to etch. Such a small thickness also reduces the costs.

On the other hand, the layer should be stable at operating temperatures of e.g. 300° C. and more and have sufficient step coverage at the location of the vias 25, for which reason the thickness of the platinum layer should advantageously be at least 10 nm, in particular at least 50 nm.

As can be seen, this allows to form vias 25 extending from the electrodes 3 to the metal layers 10 of the CMOS circuitry. The upper section 24 of these vias 25 is of platinum and whose lower section 23 is of tungsten. In FIG. 6, upper section 24 has a height exceeding the height (thickness) of the platinum layer elsewhere, but it may also have the same height as the platinum layer elsewhere.

The thickness of the electrodes is in the range of 50 to 300 nm, in particular in the range of 50 to 120 nm.

Figure 7:
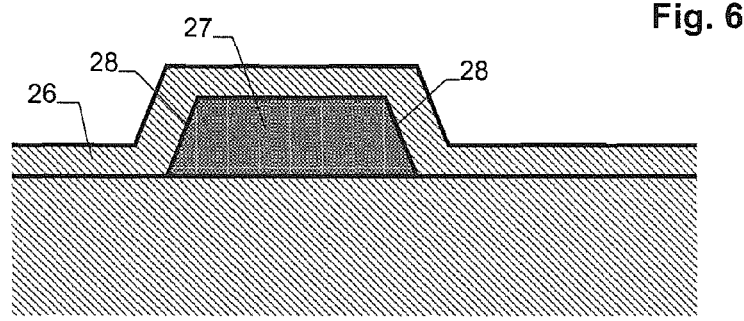
FIG. 7 shows a sectional view of a structure of the platinum layer and the cover layer.

Finally, a protective dielectric cover layer 26 is applied over the device. This is illustrated schematically in FIG. 7. As can be seen, using reactive ion etching for forming the structures 27 in the platinum layer allows to form the tapered structures with inclined edges 28, which simplifies the application of the advantageously thin protective layer 26.

Once that the metal and dielectric structures on the top side of the device are complete, opening 12 is etched from the bottom side, e.g. using a plasma process (such as deep reactive ion etching) or a wet process (such as anisotropic etching using KOH) after application of a photolithographic mask to bottom side 7 of substrate 1.

Now, patch 2 of the sensing material can be applied to the top of membrane 13, thereby forming the device shown in FIGS. 1 and 2.

Notes:

In the embodiment described above, the sensor device was a gas sensor having a metal-oxide, in particular tin oxide, as sensing material. The device can, however, also use another sensing material as known to the skilled person.

In summary, in one embodiment, a CMOS gas sensor is described, which comprises a membrane 13 extending over an opening 12 of a silicon substrate 1. A patch 2 of sensing material is arranged on the membrane 13 and in contact with electrodes 3 of platinum. A heater 5 of tungsten is located in or on the membrane 13 at the location of the patch 2 of metal-oxide sensing material. Combining platinum electrodes 3 with a tungsten heater 5 on top of a CMOS structure provides a gas sensor of high reliability and stability.

While there are shown and described presently preferred embodiments of the invention, it is to be distinctly understood that the invention is not limited thereto but may be otherwise variously embodied and practised within the scope of the following claims.

The invention claimed is:

1. A gas sensor comprising
a silicon substrate,
CMOS circuitry integrated on said silicon substrate,
an opening extending through said substrate,
a membrane extending over said opening,
a patch of sensing material arranged on said membrane,
electrodes arranged on said membrane in electrical contact with said patch of sensing material,
a tungsten heater arranged in or on said membrane at a location of said patch,
wherein,
said electrodes are of platinum, and
the gas sensor further comprises at least one via extending from said electrodes to said CMOS circuitry, wherein said via is formed in a lower section of tungsten and in an upper section of platinum.

2. The gas sensor of claim 1 further comprising a platinum temperature sensor arranged on said membrane.

3. The gas sensor of claim 1 further comprising at least one heat spreading structure of platinum or tungsten, in addition to said electrodes and said heater, arranged at the location of said patch, and in particular wherein said heat spreading structure does not extend over an edge of said membrane.

4. The gas sensor of claim 1 wherein said CMOS circuitry comprises a plurality of metal layers, wherein said tungsten heater and said electrodes are arranged at a level higher than metal layers.

5. The gas sensor of claim 1 wherein said heater is formed and structured out of a layer of tungsten, said electrodes are formed and structured out of a layer of platinum, and said at least one via is structured out of the same tungsten layer and the same platinum layer as used to form the tungsten heater and the platinum electrodes, respectively.

6. The gas sensor of claim 1 wherein said electrodes have a thickness of less than 200 nm, in particular of less than 100 nm.

7. The gas sensor of claim 1 wherein said tungsten heater has a thickness of at least 150 nm.

8. A method for manufacturing the gas sensor of claim 1, the method comprising:
   forming said tungsten heater by depositing and structuring a layer of tungsten and
   forming said electrodes and said at least one via by depositing and structuring a layer of platinum, so as for said at least one via to extend from said electrodes to said CMOS circuitry, wherein,
   said at least one via is formed in a lower section of tungsten and in an upper section of platinum.

9. The method of claim 8 comprising the step of forming said electrodes, said upper section of said at least one via and a platinum temperature sensor by structuring said layer of platinum.

10. The method of claim 8 wherein said layer of platinum is applied by sputtering.

11. The method of claim 8 wherein said layer of platinum is structured with inclined edges using reactive ion etching or lift-off techniques and wherein a cover layer is applied over the platinum layer.

12. The method of claim 8 wherein said tungsten heater is formed by the steps of
   forming trenches in a surface of said substrate,
   applying said layer of tungsten to said surface, and
   removing said layer of tungsten where it does not extend into the trenches.

13. The method of claim 12 wherein said step of removing said layer of tungsten is carried out by polishing said layer of tungsten.

14. The method of claim 8 wherein said layer of tungsten is formed by chemical vapor deposition.

15. The method of claim 8, wherein:
   forming said tungsten heater further comprises forming said lower section of said at least one via, by depositing and structuring a layer of tungsten and
   forming said electrodes further comprises forming said upper section of said at least one via, by depositing and structuring a layer of platinum.

\* \* \* \* \*